(12) United States Patent
Huang et al.

(10) Patent No.: US 11,920,996 B2
(45) Date of Patent: Mar. 5, 2024

(54) CUSTOMIZABLE PRESSURE SENSOR ARRAY

(71) Applicant: CASE WESTERN RESERVE UNIVERSITY, Cleveland, OH (US)

(72) Inventors: Ming-Chun Huang, Cleveland, OH (US); Diliang Chen, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 824 days.

(21) Appl. No.: 16/976,675

(22) PCT Filed: Mar. 11, 2019

(86) PCT No.: PCT/US2019/021637
§ 371 (c)(1),
(2) Date: Aug. 28, 2020

(87) PCT Pub. No.: WO2019/173827
PCT Pub. Date: Sep. 12, 2019

(65) Prior Publication Data
US 2021/0048358 A1 Feb. 18, 2021

Related U.S. Application Data

(60) Provisional application No. 62/641,068, filed on Mar. 9, 2018.

(51) Int. Cl.
*A61B 5/11* (2006.01)
*G01L 5/00* (2006.01)
*G01L 5/10* (2020.01)

(52) U.S. Cl.
CPC ............ *G01L 5/0019* (2013.01); *A61B 5/112* (2013.01); *G01L 5/10* (2013.01)

(58) Field of Classification Search
CPC ......... G01L 5/0019; G01L 5/10; G01L 1/205; A61B 5/112; A61B 5/6807; A61B 2562/0247; A61B 5/1038; A61B 5/1117
See application file for complete search history.

(56) References Cited

U.S. PATENT DOCUMENTS 5,033,291 A * 7/1991 Podoloff .................. G01L 1/205
73/172
5,323,650 A * 6/1994 Fullen .................. A61B 5/1036
600/592

(Continued)

OTHER PUBLICATIONS

Hanna Yousef, Mehdi Boukallel, and Kaspar Althoefer. Tactile sensing for dexterous in-hand manipulation in roboticsa review. Sensors and Actuators A: physical, 167(2):171-187, 2011.

(Continued)

*Primary Examiner* — David J Bolduc
(74) *Attorney, Agent, or Firm* — TAROLLI, SUNDHEIM, COVELL & TUMMINO, LLP

(57) ABSTRACT

A pressure sensor array can be used to record a pressure distribution in gait analysis and/or tactile sensing applications. The pressure sensor array can include a piezo-resistive material and a uniform distribution of a plurality of flexible circuits. Each of the plurality of flexible circuits comprise at least one wire connecting an internal portion of a respective flexible circuit to a common port. A device housing the pressure sensor array can be customized to a size and used for a gait analysis and/or tactile sensing application. The arrangement of the wiring permits partial sensors to be used as part of the pressure sensor array during the gait analysis and/or tactile sensing application.

13 Claims, 9 Drawing Sheets

(56) References Cited

U.S. PATENT DOCUMENTS

| | | | | |
|---|---|---|---|---|
| 5,678,448 | A * | 10/1997 | Fullen | A61B 5/1036 600/592 |
| 6,155,120 | A * | 12/2000 | Taylor | A61B 5/1036 73/862.046 |
| 6,195,921 | B1 * | 3/2001 | Truong | A43B 3/00 36/137 |
| 7,426,873 | B1 * | 9/2008 | Kholwadwala | A43B 3/00 73/818 |
| 9,192,816 | B2 | 11/2015 | Molyneux et al. | |
| 9,568,381 | B2 | 2/2017 | Daniecki et al. | |
| 10,959,644 | B2 * | 3/2021 | Reese | A61B 5/6807 |
| 11,044,967 | B2 * | 6/2021 | Walker | G01L 5/24 |
| 2007/0282562 | A1 * | 12/2007 | Schwartz | A43D 1/025 702/139 |
| 2009/0183388 | A1 * | 7/2009 | Miller | A43D 1/02 36/43 |
| 2010/0152619 | A1 | 6/2010 | Kalpaxis et al. | |
| 2013/0019694 | A1 | 1/2013 | Molyneux et al. | |
| 2013/0096466 | A1 * | 4/2013 | Sarrafzadeh | A61B 5/7225 600/592 |
| 2014/0182170 | A1 * | 7/2014 | Wawrousek | A43B 5/02 702/155 |
| 2014/0276236 | A1 * | 9/2014 | Swain | A61B 5/1038 600/592 |
| 2015/0330855 | A1 | 11/2015 | Daniecki et al. | |
| 2015/0351493 | A1 * | 12/2015 | Ashcroft | A43B 5/02 36/132 |
| 2016/0287937 | A1 * | 10/2016 | Fitzgerald | G09B 19/0038 |
| 2016/0299021 | A1 * | 10/2016 | Thillainadarajah | A43B 17/00 |
| 2016/0335913 | A1 * | 11/2016 | Grant | B32B 15/14 |
| 2017/0027512 | A1 | 2/2017 | Yuan et al. | |
| 2017/0265582 | A1 * | 9/2017 | Walker | G05B 15/02 |
| 2017/0265584 | A1 * | 9/2017 | Walker | A43C 11/008 |
| 2019/0175070 | A1 * | 6/2019 | Decker | A43D 1/02 |
| 2019/0307583 | A1 * | 10/2019 | Herr | A61H 3/00 |

OTHER PUBLICATIONS

Takao Someya, Tsuyoshi Sekitani, Shingo Iba, Yusaku Kato, Hiroshi Kawaguchi, and Takayasu Sakurai. A large-area, flexible pressure sensor matrix with organic field-effect transistors for artificial skin applications. Proceedings of the National Academy of Sciences of the United States of America, 101(27):9966-9970, 2004.

Jason J Liu, Ming-Chun Huang, Wenyao Xu, and Majid Sarrafzadeh. Bodypart localization for pressure ulcer prevention. In Engineering in Medicine and Biology Society (EMBC), 2014 36th Annual International Conference of the IEEE, pp. 766-769. IEEE, 2014.

Wenyao Xu, Ming-Chun Huang, Navid Amini, Jason J Liu, Lei He, and Majid Sarrafzadeh. Smart insole: A wearable system for gait analysis. In Proceedings of the 5th International Conference on PErvasive Technologies Related to Assistive Environments, p. 18. ACM, 2012.

Jiawei Cui, Jia Chen, Guanzhou Qu, James Starkman, Xiao Zeng, Elizabeth Madigan, Miriam Pekarek, Wenyao Xu, and Ming-Chun Huang. Wearable gait lab system providing quantitative statistical support for human balance tests. Smart Health, 2017.

D. Chen, J. Chen, H. Jiang, and M. C. Huang. Risk factors identification for work-related musculoskeletal disorders with wearable and connected gait analytics system. In 2017 IEEE/ACM International Conference on Connected Health: Applications, Systems and Engineering Technologies (CHASE), pp. 330-339, Jul. 2017.

Feng Lin, Xiaowei Xu, Aosen Wang, Lora Cavuoto, and Wenyao Xu. Automated patient handling activity recognition for at-risk caregivers using an unobtrusive wearable sensor. In Biomedical and Health Informatics (BHI), 2016 IEEE-EMBS International Conference on, pp. 422-425. IEEE, 2016.

Wenyao Xu, Ming-Chun Huang, Navid Amini, Lei He, and Majid Sarrafzadeh. ecushion: A textile pressure sensor array design and calibration for sitting posture analysis. IEEE Sensors Journal, 13(10):3926-3934, 2013.

Tim Dumbleton, Arjan WP Buis, Angus McFadyen, Brendan F McHugh, Geoff McKay, Kevin D Murray, and Sandra Sexton. Dynamic interface pressure distributions of two transtibial prosthetic socket concepts. Journal of Rehabilitation Research & Development, 46(3), 2009.

Lin Shu, Tao Hua, Yangyong Wang, Qiao Li, David Dagan Feng, and Xiaoming Tao. In-shoe plantar pressure measurement and analysis system based on fabric pressure sensing array. IEEE Transactions on Information Technology in Biomedicine, 14(3):767-775, 2010.

Richard E Fan, Martin O Culjat, Chih-Hung King, Miguel L Franco, Richard Boryk, James W Bisley, Erik Dutson, and Warren S Grundfest. A haptic feedback system for lower-limb prostheses. IEEE Transactions on Neural Systems and Rehabilitation Engineering, 16(3):270-277, 2008.

Jacqueline J Wertsch, John G Webster, and Willis J Tompkins. A portable insole plantar pressure measurement system. Journal of rehabilitation research and development, 29(1):13, 1992.

SMM De Rossi, T Lenzi, N Vitiello, M Donati, A Persichetti, F Giovacchini, F Vecchi, and MC Carrozza. Development of an in-shoe pressure-sensitive device for gait analysis. In Engineering in Medicine and Biology Society, EMBC, 2011 Annual International Conference of the IEEE, pp. 5637-5640. IEEE, 2011.

Adin Ming Tan, Franz Konstantin Fuss, Yehuda Weizman, Ydwer Woudstra, and Olga Troynikov. Design of low cost smart insole for real time measurement of plantar pressure. Procedia Technology, 20:117-122, 2015.

Tekscan. F-scan in-shoe analysis system. 2017.

Hong Liu, Yuan-Fei Zhang, Yi-Wei Liu, and Ming-He Jin. Measurement errors in the scanning of resistive sensor arrays. Sensors and Actuators A: Physical, 163(1):198-204, 2010.

Jianfeng Wu, Yu Wang, Jianqing Li, and Aiguo Song. A novel two-wire fast readout approach for suppressing cable crosstalk in a tactile resistive sensor array. Sensors, 16(5):720, 2016.

Fabian Castro, Thiago Pentiado, Jorge Blanco, Ricardo Xavier, Marcelo Sanches, and Aparecido de Carvalho. Crosstalk error analysis in iidfc readout circuit for use in piezoresistive composite. IEEE Sensors Journal, 18(1):382-389, 2018.

JianFeng Wu, Lei Wang, and JianQing Li. Design and crosstalk error analysis of the circuit for the 2-d networked resistive sensor array. IEEE Sensors Journal, 15(2):1020-1026, 2015.

Feng Lin, Aosen Wang, Yan Zhuang, Machiko R Tomita, and Wenyao Xu. Smart insole: A wearable sensor device for unobtrusive gait monitoring in daily life. IEEE Transactions on Industrial Informatics, 12(6):2281-2291, 2016.

EeonTex. Eeontex nonwoven pressure sensing fabric. https://www.hitek-ltd.co.uk/index.php/downloads/dl/file/id/8740/product/0/eeontex_nw_170_slpa_2k_2015.pdf. Accessed Jan. 11, 2018.

S Santosh Kumar and BD Pant. Design principles and considerations for the idealsilicon piezoresistive pressure sensor: a focused review. Microsystem technologies, 20(7):1213-1247, 2014.

JH Kim, Kyung Tea Park, Hyeon Cheol Kim, and Kukjin Chun. Fabrication of a piezoresistive pressure sensor for enhancing sensitivity using silicon nanowire. In Solid-State Sensors, Actuators and Microsystems Conference, 2009. Transducers 2009. International, pp. 1936-1939. IEEE, 2009.

Jiahong Zhang, Yang Zhao, Yixian Ge, Min Li, Lijuan Yang, and Xiaoli Mao. Design optimization and fabrication of high-sensitivity soi pressure sensors with high signal-to-noise ratios based on silicon nanowire piezoresistors. Micromachines, 7(10):187, 2016.

Jacquelin Perry, Jon R Davids, et al. Gait analysis: normal and pathological function. Journal of Pediatric Orthopaedics, 12(6):815, 1992.

Kyoungchul Kong and Masayoshi Tomizuka. Smooth and continuous human gait phase detection based on foot pressure patterns. In Robotics and Automation, 2008. ICRA 2008. IEEE International Conference on, pp. 3678-3683. IEEE, 2008.

EeonTex. Eeontex conductive nonwoven fabric. https://cdn.sparkfun.com/datasheets/E-Textiles/Materials/NW170-PI-20%20TDS.pdf. Accessed Jan. 11, 2018.

Statex. Conductive sewing thread. https://www.sparkfun.com/datasheets/E-Textiles/260151023534oz.pdf. Accessed Jan. 11, 2018.

(56) References Cited

OTHER PUBLICATIONS

Bare Conductive. Bare paint technical data sheet. https://cdn.sparkfun.com/datasheets/E-Textiles/Materials/TechnicalDataSheetBareConductivePaint.pdf. Accessed Jan. 11, 2018.

Yeoh H T, Lockhart T E, Wu X. Non-fatal occupational falls on the same level[J]. Ergonomics, 2013, 56(2): 153-165.

Bureau of Labor Statistics. [Accessed Dec. 24, 2011] Census of Fatal Occupational Injuries (Preliminary Results). 2010a. [online]. Available from: http://www.bls.gov/news.release/pdf/cfoi.pdf.

Bureau of Labor Statistics. [Accessed Dec. 24, 2011] Nonfatal Occupational Injuries and Illnesses, Private Industry Case and Demographics. 2008. [online]. Available from: http://stats.bls.gov/iif/oshwc/osh/case/osch0040.pdf.

Yoon H Y, Lockhart T E. Nonfatal occupational injuries associated with slips and falls in the United States[J]. International journal of industrial ergonomics, 2006, 36(1): 83-92.

Liberty Mutual Research Institute for Safety. 2014. "2014 Liberty Mutual Workplace Safety Index."

Liberty Mutual Research Institute for Safety. 2017. 2017 Liberty Mutual Workplace Safety Index.

Englander F, Hodson T J, Terregrossa R A. Economic dimensions of slip and fall injuries[J]. Journal of Forensic Science, 1996, 41(5): 733-746.

Howell A M, Kobayashi T, Hayes H A, et al. Kinetic gait analysis using a low-cost insole[J]. IEEE Transactions on Biomedical Engineering, 2013, 60(12): 3284-3290.

Morris S J, Paradiso J A. Shoe-integrated sensor system for wireless gait analysis and realtime feedback[C]// Engineering in Medicine and Biology, 2002. 24th Annual Conference and the Annual Fall Meeting of the Biomedical Engineering Society EMBS/BMES Conference, 2002. Proceedings of the Second Joint. IEEE, 2002, 3: 2468-2469.

Bamberg S J M, Benbasat A Y, Scarborough D M, et al. Gait analysis using a shoeintegrated wireless sensor system [J]. IEEE transactions on information technology in biomedicine, 2008, 12(4): 413-423.

Lockhart T E. "Biomechanics of Human Gait-Slip and Fall Analysis", Encyclopedia of Forensic Sciences, 2nd Edition, JA Siegel, PJ Saukko (eds.), 2013 Academic Press.

Applicant: Case Western Reserve University; International Application No. PCT/US2019/21637; Filed: Mar. 11, 2019; Title: Customizable Pressure Sensor Array; PCT International Search Report; Authorized Officer: Shane Thomas; Date of Completion: May 9, 2019; 8 pgs.

* cited by examiner

CUSTOMIZABLE PRESSURE SENSOR ARRAY

CROSS-REFERENCE TO RELATED APPLICATION

This application claims the benefit of U.S. Provisional Application Ser. No. 62/641,068, filed Mar. 9, 2018, entitled "CUSTOMIZABLE PRESSURE SENSOR ARRAY", the entirety of which is hereby incorporated by reference for all purposes.

GOVERNMENT SUPPORT

This invention was made with government support under Grant No. 1664368, awarded by The National Science Foundation. The United States government has certain rights in the invention.

TECHNICAL FIELD

This disclosure generally relates to pressure sensing and, more specifically, to a pressure sensor array that can be customized to different sizes without sacrificing pressure sensing ability.

BACKGROUND

Slip and falls are a leading cause of preventable workplace accidents. These preventable workplace accidents may be reduced with a better understanding of the biomechanics of the human gait under workplace conditions that can be learned by gait analysis. Camera-based assessment systems are commonly used for gait analysis, but workplace environments have poor lighting and multiple visual barriers making camera-based assessment systems impractical. An alternate solution involves continuous monitoring of pressure using an array of pressure sensors (or "pressure sensor array", a group of pressure sensors, which can be deployed in a certain geometry pattern and used for recording pressure signals) placed in a shoe insole. While such pressure sensor arrays can be used for continuous monitoring of gait information in most workplace conditions, these pressure sensor arrays do not allow for customization of the insole size, since trimming the insole destroys the pressure sensor arrays. For pressure sensor arrays to be used in shoes for gait analysis, insoles must be made to fit different foot sizes, which increases the cost of manufacturing, making the use of pressure sensor arrays cost prohibitive in monitoring gait analysis in workplace slip and fall conditions.

SUMMARY

In an aspect, a system that includes a device housing a pressure sensor array is described. The pressure sensor array includes a piezo-resistive material and a uniform distribution of a plurality of flexible circuits. Each of the plurality of flexible circuits includes at least one wire connected to a common port. The device and the pressure sensor array are customizable to different sizes for gait analysis and/or tactile sensing applications. Each of the at least one wire from each of the plurality of flexible circuits is positioned to ensure that each of the plurality of flexible circuits is connected to the common port even when customized so that every one of the plurality of flexible circuits remaining on the sensor array as full flexible circuits and partial flexible circuits is usable after the pressure sensor array is customized.

In another aspect, a method that uses the device housing the pressure sensor array is described. The device housing the pressure sensor array can be customized to a size. The pressure sensor array includes a piezo-resistive material and a uniform distribution of a plurality of flexible circuits, and each of the plurality of flexible circuits includes at least one wire connecting an internal portion of a respective flexible circuit to a common port. The customized pressure sensor array can be used for a gait analysis and/or tactile sensing application.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

This disclosure describes a customizable pressure sensor array that can be customized to different sizes without sacrificing pressure sensing ability (for example, a "trimmable pressure sensor array" that can be altered, cut, trimmed, or the like, to different sizes). Such trimmable pressure sensor arrays that can be cut into different sizes without losing sensing resolution are particularly well suited for gait analysis and/or other tactile sensing applications. In an example gait analysis application, a shoe insole (or insert, bottom, or the like) can be used with a pressure sensor array in a certain geometry within the shoe insole. Such pressure sensor arrays can be used for continuous monitoring of gait information in most workplace conditions; however, traditional pressure sensor arrays do not allow for customization of the insole size, since trimming the insole destroys the pressure sensor arrays. The customizable pressure sensor arrays of the present disclosure can be fit inside customizable insoles (or insert, bottom, or the like—any part of the shoe that can be customized to different sizes), which can be customized for different foot sizes.

Making a single-sized insole housing a customizable pressure sensor array can decrease the cost of manufacturing, making the use of pressure sensor arrays no longer cost prohibitive in performing gait analysis in workplace slip and fall conditions. The customizable pressure sensor array is not limited to applications in customizable shoe insoles. For example, the customizable pressure sensor array can be housed within any type of body molding housing that can mold to any portion of a user's body and used in a tactile sensing application. The term "user" is synonymous with the terms "subject" and "patient" and refers to a bipedal animal, like a human.

Figure 1:
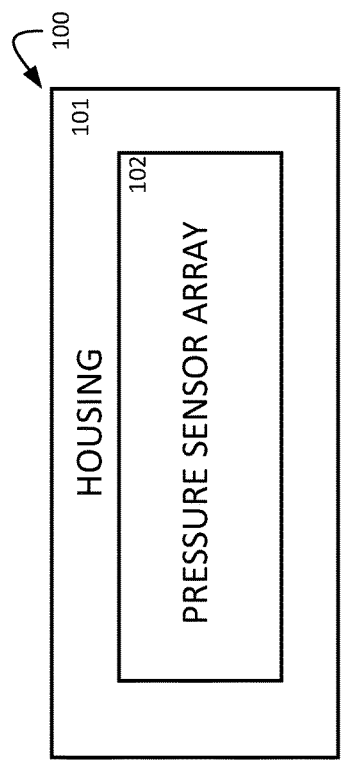
FIG. 1 illustrates an example of a system that includes a customizable pressure sensor array enclosed in a customizable housing.

FIG. 1 illustrates an example of a system 100 that includes a customizable pressure sensor array 102 enclosed in a customizable housing 101. The customizable housing 101 can be made of any material that can hold the pressure sensor array 102 therein. For example, the customizable housing 101 may be any type of body molding material that can mold to any portion of a user's body, but still be customized to size (e.g., a fabric, a polymer, and/or the like). As another example, the customizable housing 101 can be a shoe insole (or insert, bottom, or the like—any part of the shoe that can be customized to different sizes). The customizable pressure sensor array 102 can include a pressure sensitive material (like a piezo-resistive material 202 or any other material that has a variable resistance that varies proportionally with an applied pressure) and one or more circuit layers (circuit layer A 201a and/or circuit layer B 201b, as illustrated). The materials used to construct the pressure sensitive material and the corresponding circuits are easily trimmed to ensure that the pressure sensor array 102 can be easily customized for different sizes to which the housing 101 is trimmed. The pressure sensitive material can be consistent such that a pressure sensitivity of any point on the material is similar to other points on the material. The corresponding circuits are designated to make sure that after being customized into different sizes, the sensor array can maintain its original resolution (the resolution of the pressure sensor array refers to the number of pressure sensors in a unit area of the pressure sensor array).

Figure 2:
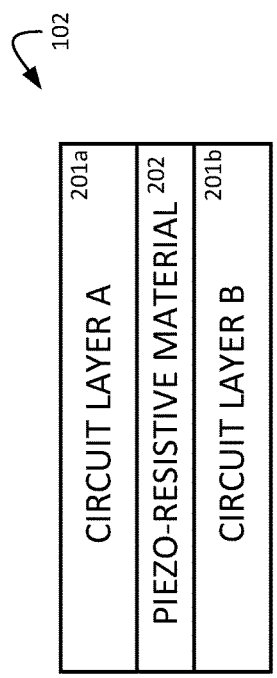
FIG. 2 illustrates an example layout of the customizable pressure sensor array shown in FIG. 1.

In the example shown in FIG. 2, the pressure sensitive material is represented as piezo-resistive material 202. The one or more circuit layers are represented as circuit layer A 201a and circuit layer B 201b, which sandwich the piezo-resistive layer 202. However, the piezo-resistive layer 202 may be contacted by only one of circuit layer A 201a and circuit layer B 201b. For example, circuit layer A 201a may be sandwiched by the piezo-resistive layer 202 and circuit layer B 201b. In another example, circuit layer B 201b can be sandwiched by circuit layer A 201a and the piezo-resistive layer. In still another example, circuit layer A 201a and circuit layer B 201b can be next to one another and each contacting the piezo-resistive material 202. Circuit layer A 201a and/or circuit layer B 201b can be placed in numerous other arrangements with the piezo-resistive layer 202. One of the circuit layers (e.g., circuit layer A 201a) can connect the piezo-resistive material 202 to a source voltage via a fixed resistance, while the other of the circuit layers (e.g., circuit layer B 201b) can connect the piezo-resistive material 202 to a ground electronic level.

Each of the one or more circuit layers (e.g., circuit layer A 201a and/or circuit layer B) can include a uniform distribution of a plurality of flexible circuits. The one or more circuit layers (e.g., circuit layer A 201a and/or circuit layer B) can be individually flexible to create a plurality of flexible circuits that are wired to a common port. As an example, the one or more circuit layers can include one or more electrical components deposited onto flexible substrates (e.g., as a flexible printed circuit board or PCB). The one or more electrical components can include pads (e.g., copper pads) and wires. The wires can connect the pads to a common port.

Figure 3:
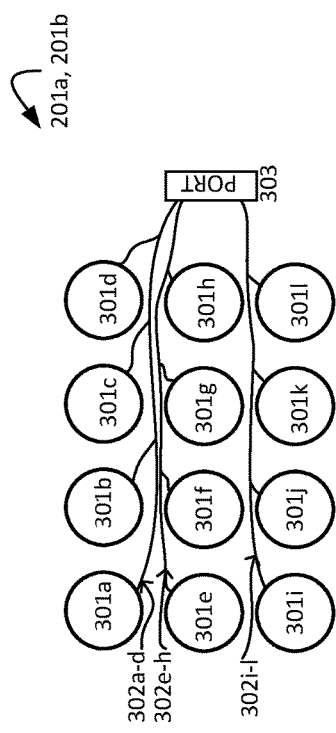
FIG. 3 illustrates an example of the copper pads and wiring of circuit layer A and/or circuit layer B in FIG. 2.

FIG. 3 is an example of circuit layer A 201a and/or circuit layer B 201b, which each include an equal number of uniformly distributed pads 301a-1. Circuit layer A 201a and/or circuit layer B 201B can include a plurality of pads (representing electrical components) 301a-1. Twelve pads are shown in FIG. 3, but this number is not limiting and is instead only exemplary. Each of the pads 301a-1 is connected to at least one wire 302a-1 (each of 302a-1 is shown as a single wire, but may each represent a plurality of wires). The wires 302a-1 can be positioned relative to the respective flexible circuit (or pad) 301a-1 to ensure that each of the plurality of flexible circuits 301a-1 is connected to the common port, even when customized so that every one of the plurality of plurality of flexible circuits 301a-1 remaining on the customized pressure sensor array as full flexible circuits and partial flexible circuits is still usable after the pressure sensor array is customized Notably, the pressure sensor array retains its original pressure sensing resolution after being customized to any number of different sizes due to the uniform distribution of flexible circuits on the one or more circuit layers (e.g., circuit layer A 201a and/or circuit layer B). As an example, each wire 302a-1 can be connected to an internal portion of the respective flexible circuit (internal meaning away from or opposite to an edge of the housing 101). The wires 302a-1 connect the pads 301a-1 to the common port 303 and transmit data from the pads 301a-1 to the common port 303, which can connect to signal processing circuitry (shown, for example, in FIG. 8).

Figure 4:
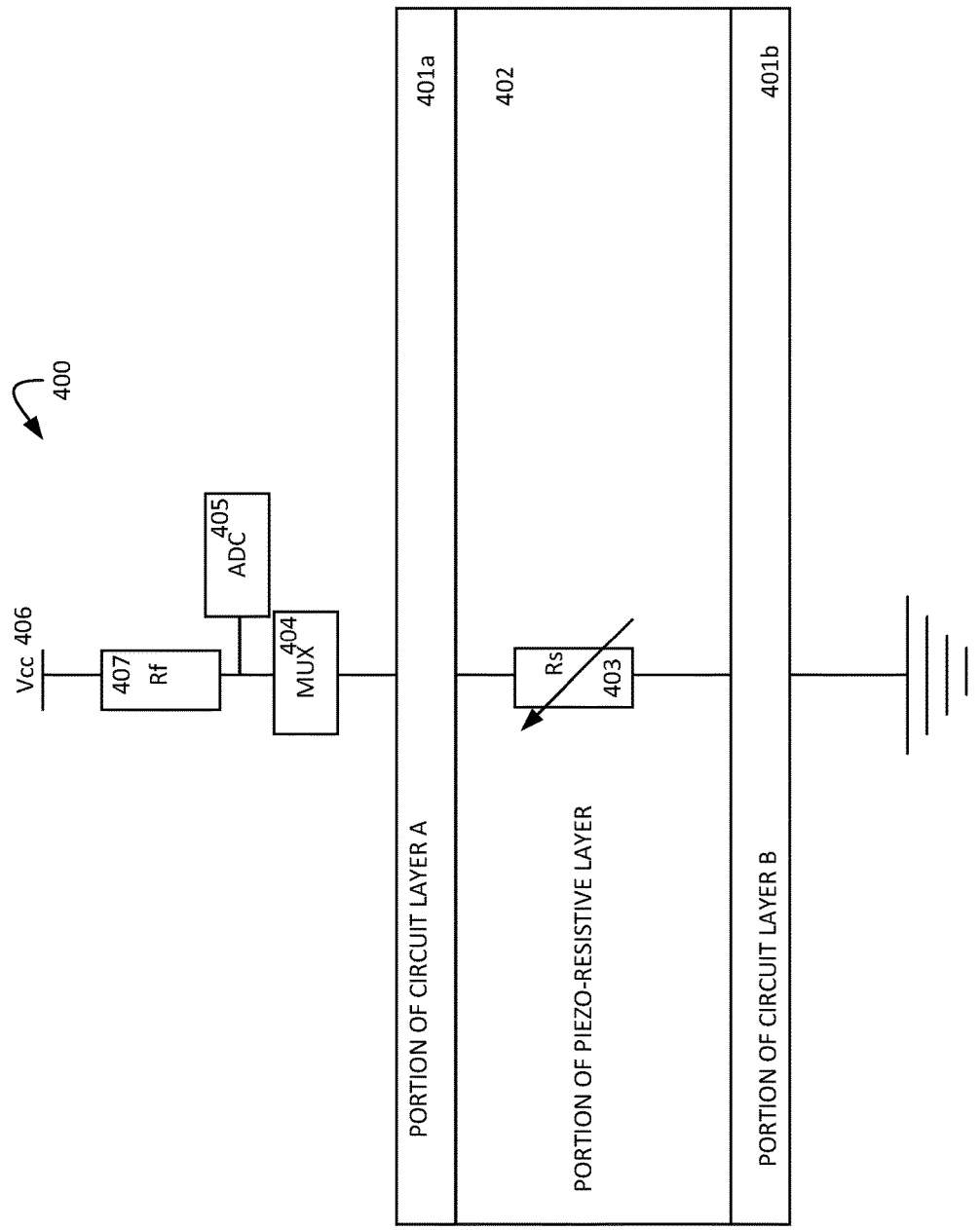
FIG. 4 illustrates the mechanism for determining a resistance of a pressure sensor of the pressure sensor array of FIG. 1.

The signal processing circuitry can receive signals from each of the wires 302a-1 and from each of circuit layer A 201a and circuit layer B 201b and determine the resistance of the piezo-resistive layer between portions of circuit layer A 201a and circuit layer B. Based on the resistance, the signal processing circuitry can determine the pressure experienced by the different portions of the piezo-resistive layer 202. The signal processing circuit can receive many inputs from many individual circuits. FIG. 4 shows a single circuit 400 (a circuit in this sense is a portion of circuit layer A 401a (or a pad), a portion of circuit layer B 401b (or a pad opposed to the pad in circuit layer A 401a), and a portion of the piezo-resistive layer 402. The piezo-resistive material within the piezo-resistive layer 402 can be modeled as a variable resistance (Rs 403) that can vary in a manner proportional (or otherwise related) to the pressure applied to the piezo-resistive material.

A portion of circuit layer B 401b can connect the portion of the piezo-resistive material 402 to the ground electronic level. A portion of circuit layer A 401a can connect the portion of the piezo-resistive material 402 to a source voltage (Vcc 406) via a fixed resistor (Rf 407). A voltage divider circuit (represented by Vcc 406, Rf 407, and MUX 404, but may include additional components) and an analog to digital convertor (ADC 405) can be used to measure the voltage drop on the pressure sensor. The resistance of the individual pressure sensor can be measured with the following Equation:

$$Rsensor = \frac{Vsensor\ Rfixed}{Vcc - Vsensor},$$

where Rsensor is the resistance of the portion of piezo-resistive material 402 (represented as Rs 403 in FIG. 4), Rfixed (represented as Rf 407 in FIG. 4) is the resistance of the fixed resistor that is used to build the voltage divider circuit, Vsensor is the voltage drop on the pressure sensor, which could be measured by ADC 405, and Vcc 406 is the source voltage. By controlling the MUX 404, all pressure sensors in the array can be scanned and a pressure map can be acquired.

Figure 5:
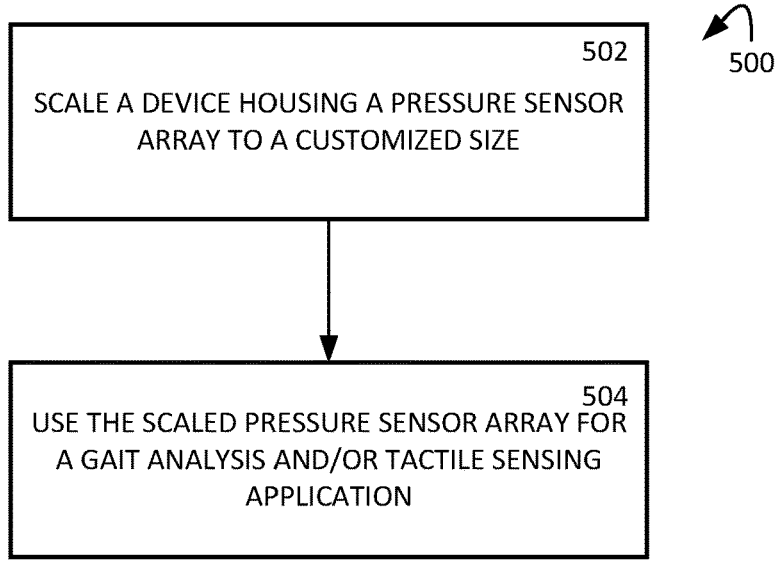
FIG. 5 illustrates a method for using a customizable pressure sensor array in a customizable device housing.
Figure 6:
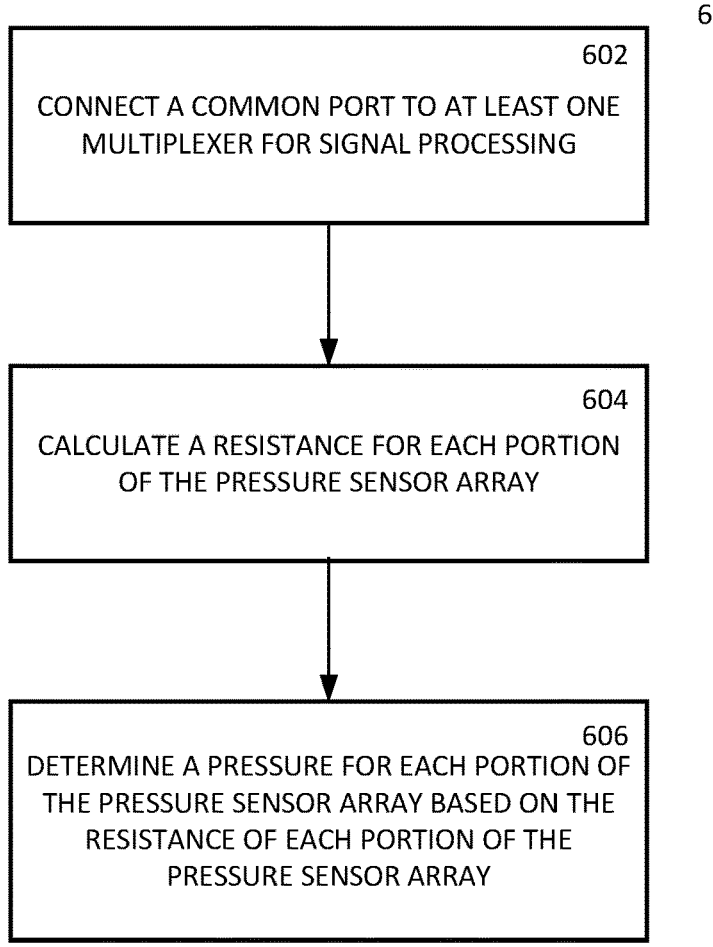
FIG. 6 illustrates a method for determining a pressure for each portion of a customizable pressure sensor array.

In view of the foregoing structural and functional features described above, example methods that can be performed by the system 100 will be better appreciated with reference to FIGS. 5-6. While, for the purposes of simplicity of explanation, the example methods of FIGS. 5-6 are shown and described as executing serially, the present examples are not limited by the illustrated order, as some actions could in other examples occur in different orders or concurrently from that shown and described herein. Moreover, it is not necessary that all described actions be performed to implement a method. One or more aspects of the methods can be stored in one or more non-transitory computer-readable media and executed by one or more processing resources, such as described herein.

FIG. 5 illustrates a method 500 for using a customizable pressure sensor array in a customizable device housing (for gait analysis or tactile sensing). At 502, a customizable device housing (e.g., housing 101) a customizable pressure sensor array (e.g., pressure sensor array 102) can be scaled (e.g., by trimming or any other type of scaling mechanism) to a size. For example, the size can be configured for a particular user. In other words, users of different sizes can each scale the device housing to the appropriate size for individual use of the device housing. At 504, the scaled pressure sensor array can be used by the particular user for a gait analysis application and/or a tactile sensing application.

FIG. 6 illustrates a method 600 for determining a pressure for each portion of a customizable pressure sensor array (e.g., a portion is shown in FIG. 4). At 602, a common port 303 can be connected to at least one multiplexer 404 for signal processing. At 604, a resistance (Rs 403) can be calculated for each portion of the pressure sensor array (as described with respect to FIG. 4). At 606, a pressure can be determined for each portion of the pressure sensor array based on the resistance of each portion of the pressure sensor array. The pressure can be displayed in a pressure map, for example.

Experimental

The following experiment shows the design and use of a customizable pressure sensor array (also referred to as a "customizable pressure sensor array") that meets the demand of being trimmed to different sizes while maintaining a sensing resolution so that accuracy is not affected by the trimming. The customizable pressure sensor array includes a piezo-resistive fabric and a plurality of flexible circuits, which are uniformly distributed. Wires on the flexible circuits were designed to ensure that all of the full/partial sensors remaining on the pressure sensor array after trimming could still be used for sensing.

Customizable Pressure Sensor Array Design

A pressure sensor array includes a plurality of pressure sensors made of a pressure sensor material and corresponding circuits with wires for transmitting data. To be customizable into different sizes according to the requirement of different users, the following requirements should be met:
 (1) The pressure sensitive material and corresponding circuits should be made of materials that are easily trimmed to ensure that the pressure sensor array can be trimmed into different sizes.
 (2) The pressure sensitive material should be consistent, so that the pressure sensitivity of any point on the pressure sensitive material is similar.
 (3) The corresponding circuits should be designed to ensure that after being cut into different sizes, the pressure sensor array could maintain its original resolution.

Pressure Sensitive Material

A commercially available piezo-resistive fabric material made by EeonTex™ was used for pressure sensitive material. Similar to normal fabric materials, the piezo-resistive fabric material is thin (with a thickness of 0.8 mm), light weight (with a weight of 170 g/m$^2$), flexible, and easily trimmed.

Corresponding Circuit Design

The circuit material of the pressure senor array is a flexible Printed Circuit Board (PCB). The flexible PCB includes a flexible, lightweight polymer (like polyimide) as the laminate material. The flexible PCB is also very thin (around 0.15 mm), so the size of the PCB is easily customizable. The customizable pressure sensor array uses the flexible PCB on the top and the bottom of the pressure sensitive material. Copper pads and wires are distributed on the flexible PCB meeting the following requirements.
 (1) The copper pads should be distributed uniformly. Since the location, shape and size of a pressure sensor are determined by the corresponding copper pads on the top and bottom layers of the sensor array, distributing the copper pads uniformly could make sure that the pressure sensors on the sensor array are uniformly distributed.
 (2) The wires should be designed to ensure that all the full/partial sensors remaining on the sensor array are connected to a common connection after the sensor array is trimmed into different sizes.

Pressure Sensor Array

Figure 7:
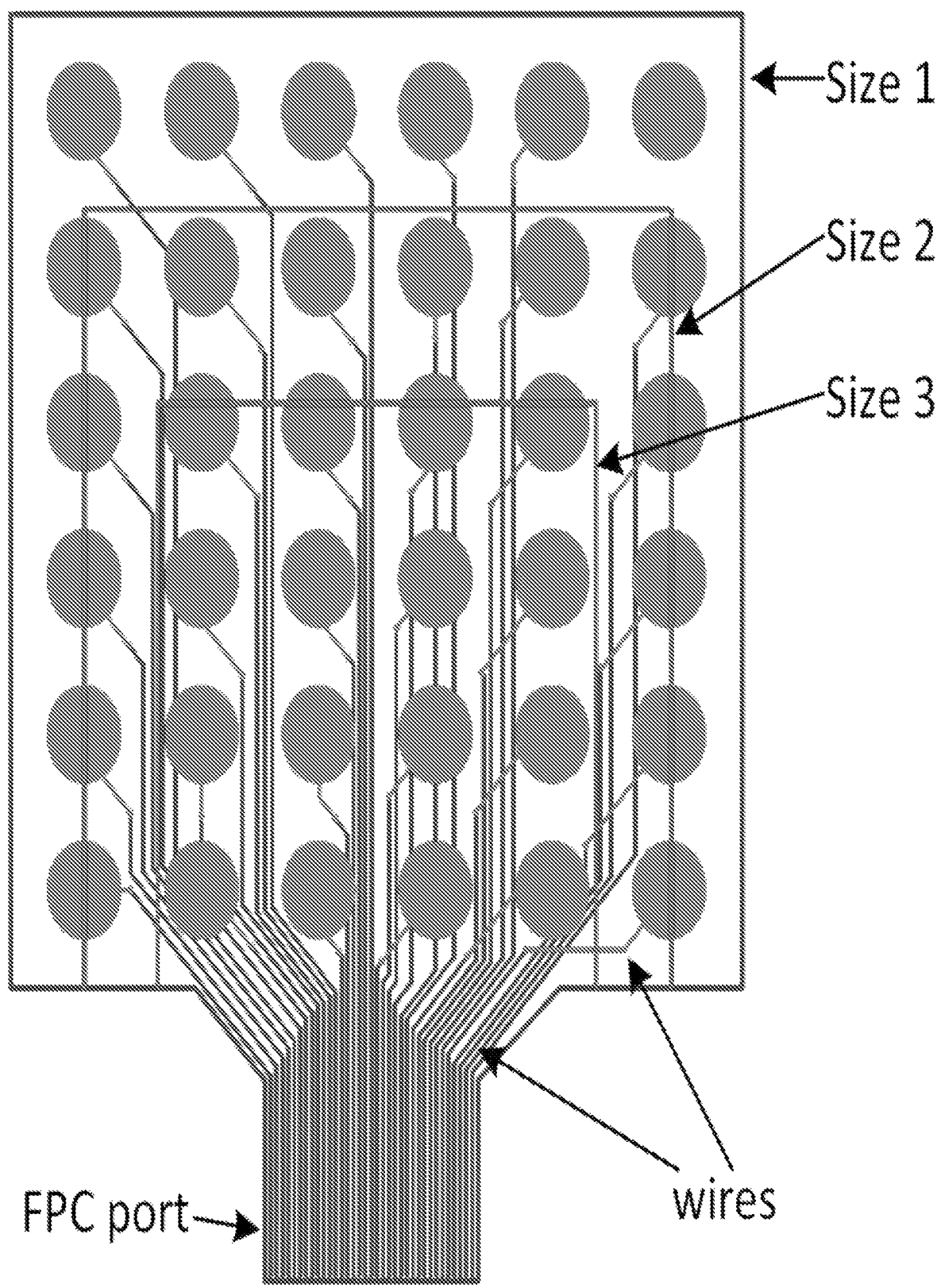
FIG. 7 illustrates an example design of the top layer of a customizable pressure sensor array.

The pressure sensor array was built with a three-layer design. The top and bottom layer each includes a plurality of corresponding circuits distributed uniformly (example of a top layer top layer shown in FIG. 7). For different applications, there might be different requirements on sensor array resolution and sensor shape and size, which could be met by configuring the distribution density, shape and size of the copper pads on the top and bottom layers. The middle layer is made of piezo-resistive material, the resistance of which is not stable but related to the applied pressure and can be modeled as a variable resistor. Therefore, through measuring the resistance of the piezo-resistive material, the force applied on it could be estimated. An example of the mechanism of measuring the resistance of the piezo-resistive material in a single pressure sensor is shown in the schematic diagram of FIG. 4. The copper pads on the bottom layer connected the piezo-resistive material to the ground electronic level, and the copper pads on the top lay connected the piezo-resistive material to the source voltage (Vcc) via a fixed resistor.

A resistance of the pressure sensor could be measured by the following Equation:

$$Rsensor = \frac{Vsensor\ Rfixed}{Vcc - Vsensor},$$

where $R_{sensor}$ is the resistance of the piezo-resistive material covered by the pair of copper pads on the top and bottom layer; $R_{fixed}$ is the resistance of the fixed resistor which is used to build a voltage divider circuit, $V_{sensor}$ is the voltage dropped on the pressure sensor; and $V_{cc}$ is the source voltage of the voltage divider circuit.

In this Example (shown schematically in FIG. 7), thirty-six (36) pressure sensors were distributed uniformly on the square sensor array. To customize the sensor array into different sizes, the user only needs to trim the sensor array. In addition, the placement of the wires with respect to the corresponding circuits can make sure that all the sensors left on the array could be connected with a common port (e.g., a FPC port), no matter to what size the pressure sensor is customized. To make the wire design more efficient, top and bottom layers of the sensor array both used two layers: one layer for distributing the copper pads, and the other layer is for routing the wires.

Signal Processing Circuit Design

Figure 8:
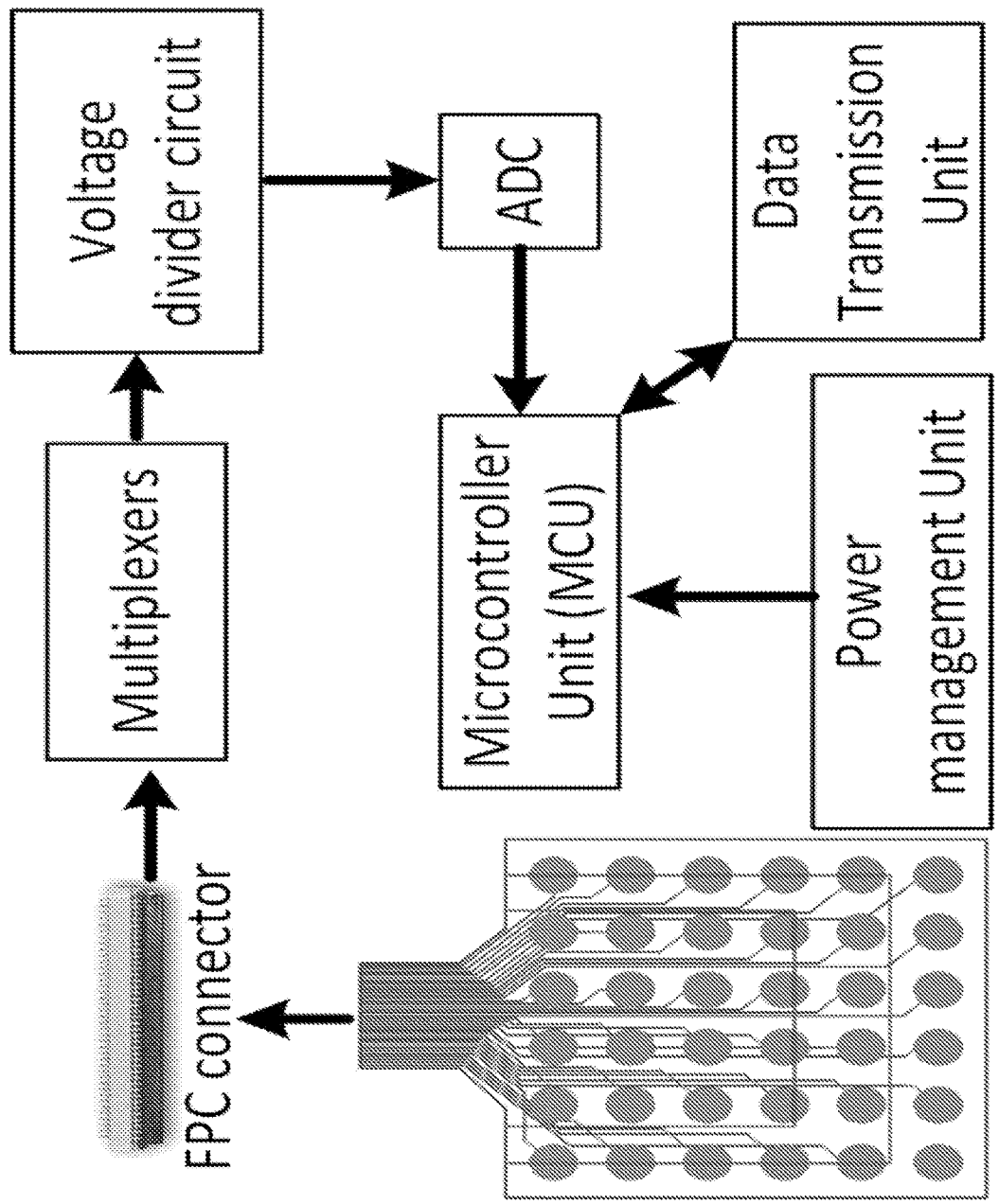
FIG. 8 illustrates an example design of the architecture of a signal processing circuit.

A signal processing circuit (for example, the FPC connector, multiplexers, voltage divider circuit, ADC, MCU, power management unit, and data transmission unit as shown in FIG. 8) measures the resistance of individual sensors within the sensor array and thereby estimate the force applied to the individual sensors. The common connector (a FPC connector) was used to electrically connect the pressure sensor array to the signal processing circuit. Multiplexers were used to connect all the pressure sensors to the voltage divider circuit, and then the voltage drop on each pressure sensor could be digitalized by an analog-to-digital convertor (ADC). For a sensor array, multiplexers are needed to connect all the pressure sensors on the sensor array to ADC. By controlling the multiplexer, all pressure sensors on the sensor array could be scanned one by one and then a pressure distribution map could be acquired. The measured data was sent out through the data transmission unit. The power management unit was used to supply suitable power to the components on circuit. The microcontroller unit (MCU) was used to control all the processes of the circuit.

Experimental Methods

Testing the Consistency of the Piezo-Resistive Material

Figure 9:
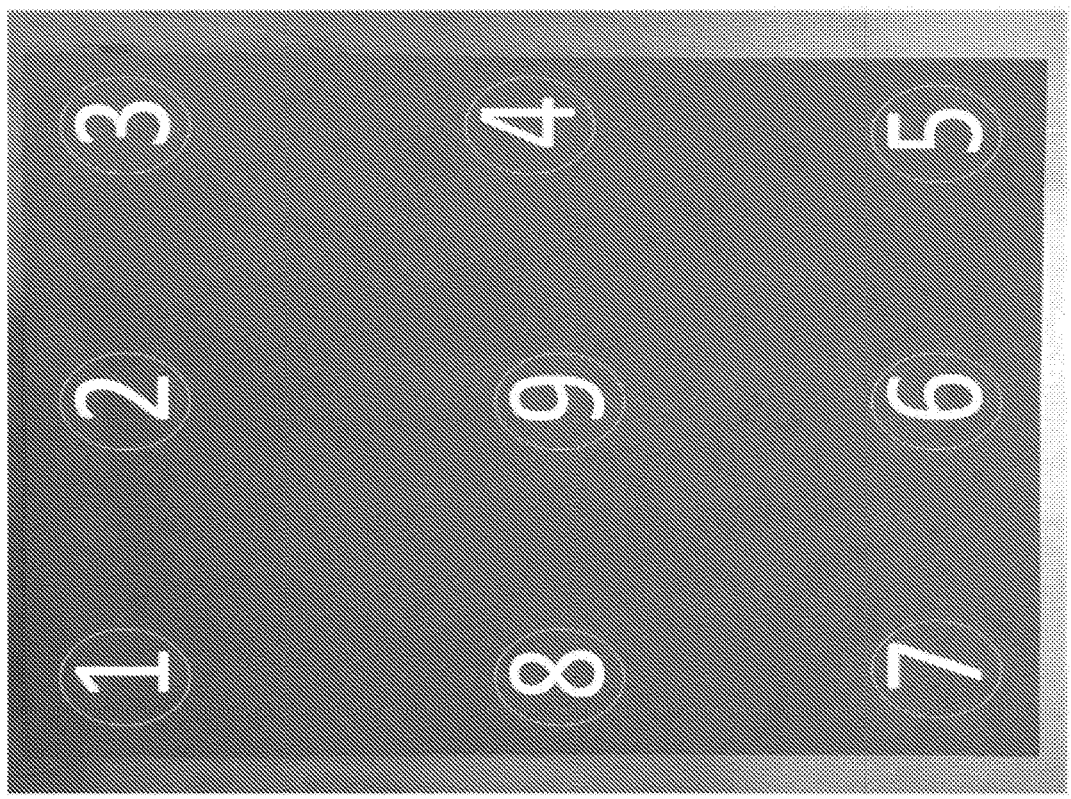
FIG. 9 illustrates locations of nine testing points for a consistency test of a piezo-electric material.

A sheet of piezo-resistive material with a dimension of 30.5×33 cm was used. As shown in FIG. 9, nine points on the margin and center areas of the sheet of piezo-resistive material were randomly selected for testing. A 130 kPa pressure was applied on each test point one by one. For each of the nine points, the resistance and the variation (the resistance difference of the test point with respect to the mean resistance of all nine points) were determined.

Testing the Influence of Trimming on the Customizable Pressure Sensor Array

Figure 11:
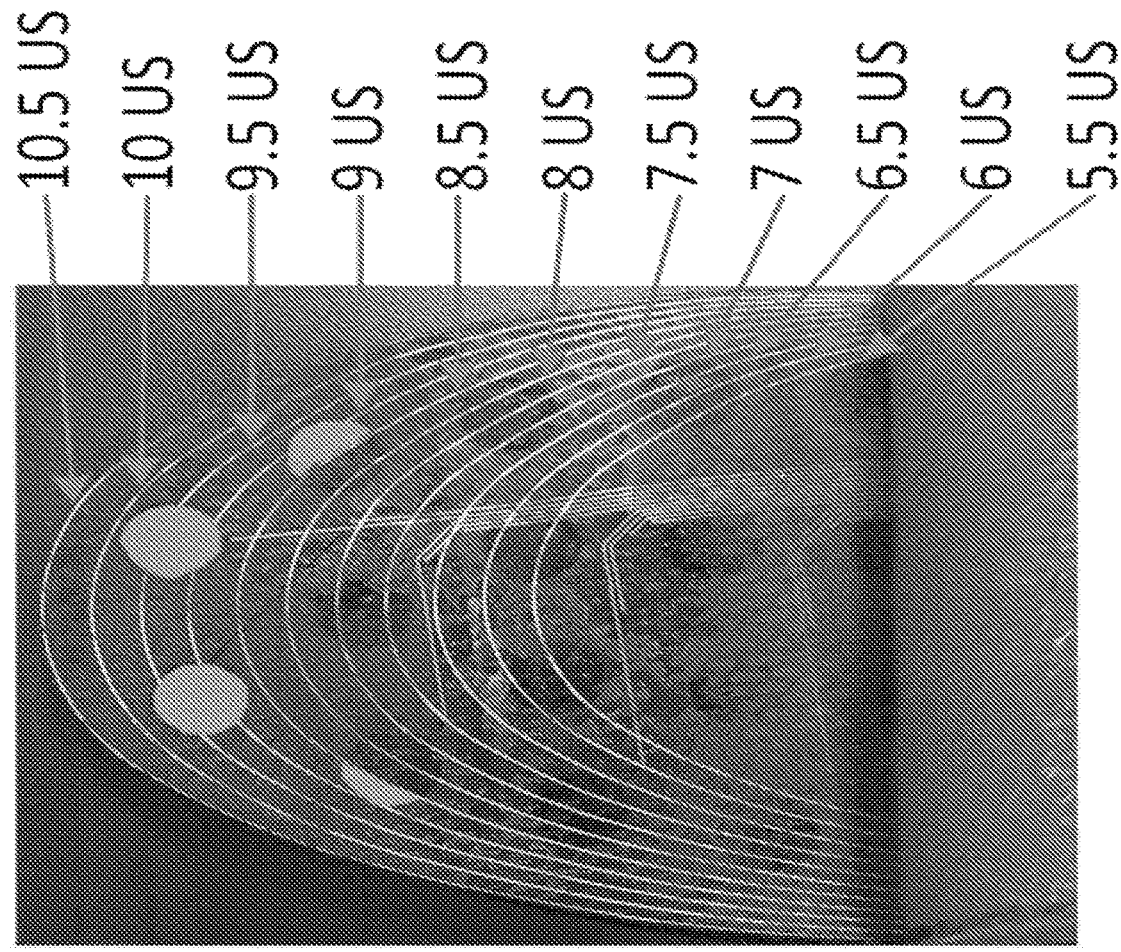
FIG. 11 illustrates individual sensors that would be cut if the insole were trimmed to 8.5 US.
Figure 10:
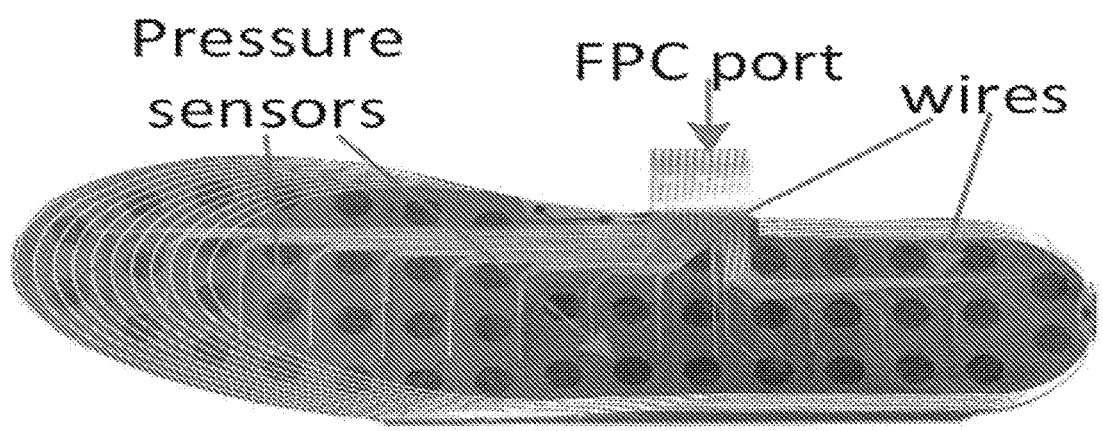
FIG. 10 illustrates an insole shaped customizable pressure sensor array.

The experiments test the influence of trimming on pressure spatial and temporal distribution patterns acquired by the customizable pressure sensor array. An insole-shaped customizable pressure sensor array was used to test the influence of trimming on the acquired pressure spatial and temporal distribution patterns (shown in FIG. 10). To make the customizable pressure sensor array fit different foot sizes, a user need only to trim the sensor array along the white line corresponding to a respective foot size (shown in FIG. 11). However, when cutting on the white lines, parts of several sensors on the edge of the customizable pressure sensor array would be cut off. However, wires on the customizable pressure sensor array connect all the full and partial sensors in the trimmed customizable pressure sensor array to the PFC port, ensuring the resolution of the customizable pressure sensor array is unchanged.

Figure 13:
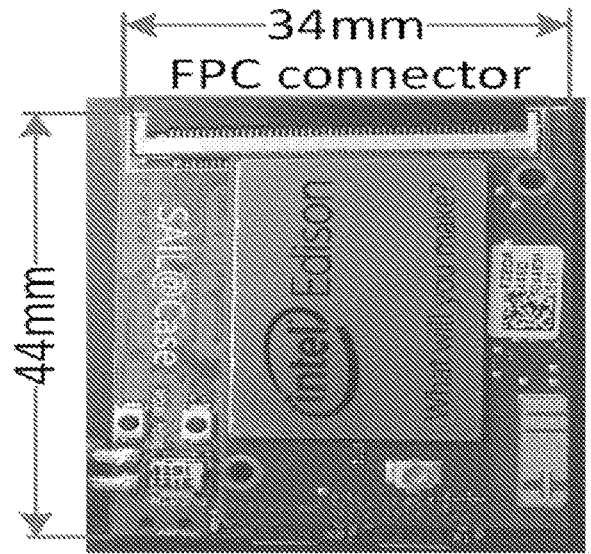
FIGS. 12 and 13 are photographs the front and back of the signal processing circuit used in the experiment.
Figure 12:
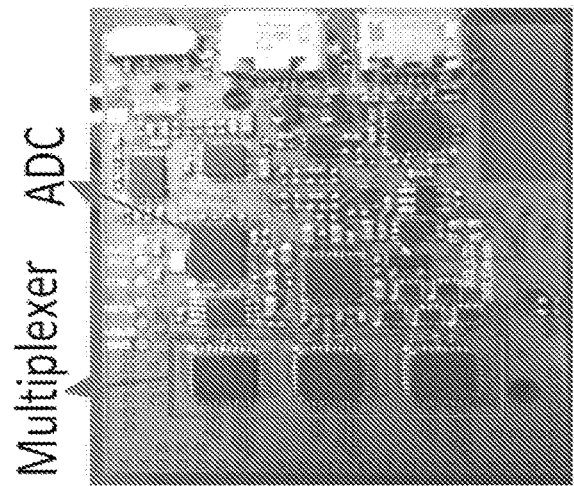
Figure 14:
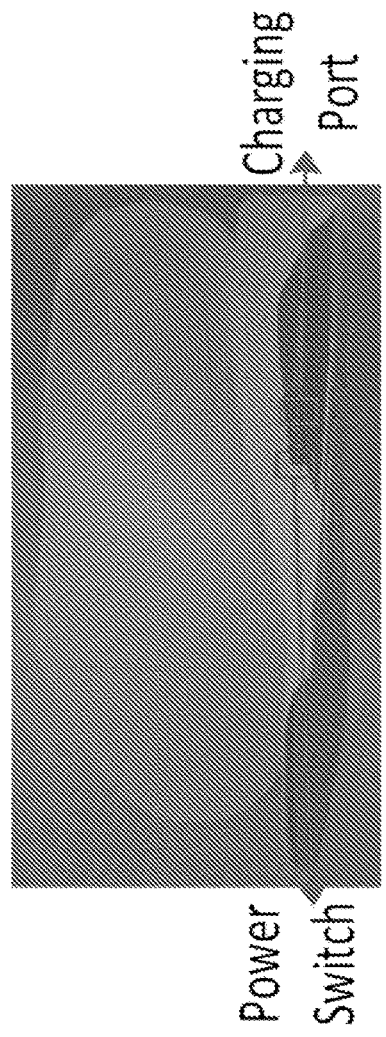
FIG. 14 is a photograph of the system prototype used in the experiment.

FIGS. 12 and 13 show details of the front and back of the signal processing circuit. The circuit board was designed in a small size (34×44×6 mm), which made it easy to be packaged in a normal insole. FIG. 14 shows a prototype of the customizable plantar pressure measurement system. In this prototype, all the circuits (i.e. signal processing circuit and customizable pressure sensor array) were packed into a normal insole.

Two gait parameters, gait cycle and cadence, were used to evaluate the customizable pressure sensor array. Experiments were designed to measure gait cycle and cadence respectively.

Gait cycle is defined as the time interval between two successive occurrences of one of the repetitive eight phases of walking (shown in FIG. 15(A)-(H)). The gait phases could be detected based on plantar pressure distribution patterns. To distinguish the eight phases from plantar pressure distribution alone, the customizable pressure sensor array was designed with high resolution and sensitivity for the pressure change under foot.

Cadence is defined as the number of steps taken in a given time (e.g., steps per minute) and can be calculated with step cycle with the following Equation:

$$\text{Cadence}\left(\frac{\text{steps}}{\text{min}}\right) = 60/StepCycle(s),$$

where StepCycle(s) is the duration time between the appearance of the same gait phase on both feet. For instance, time duration of the appearance of "initial contact" on the left foot and the next "initial contact" gait phase on the right foot is one step cycle. Since, trimming mainly influenced the sensors on the forefoot area, the cadence calculated with the "pre-swing" phase of each foot was used to evaluate the customizable pressure sensor array.

Two subjects with normal gait, foot size of 10.5 US and foot size 8.5 US, were involved in the experiment. The subject with a foot size of 10.5 US used the full size pressure sensor array. The other subject with a foot size of 8.5 US used a smaller pressure sensor array trimmed from the full size pressure sensor array. During the experiments, each subject wore the corresponding pair of insoles for plantar pressure recording.

For the experiment about gait cycle, each subject was asked to walk normally for five steps. During the experiment, one camera was used to tape the walking activities, from which eight gait phases of one gait cycle would be extracted. The other camera was used to record both the activity of the subject and the timestamp of the real-time plantar pressure data, which was used to realize the time synchronization between the taped activity video and plantar pressure data. After time synchronization, the plantar pressure distribution map of each posture in the taped video could be localized. In the experiment about cadence, each subject was asked to walk in three different cadences: 50, 60 and 70 beats per minute (BPM), respectively. A beep sound was used in the experiment to help the subject walk in the correct cadence. Before each experiment, the subject would walk with the beep sound for three minutes to be adaptive to that walking cadence. During the experiment, the subject would walk for 30 seconds with the beep sound. A rest time of 5 minutes was scheduled between experiments.

Experimental Results

Testing the Consistency of the Piezo-Resistive Material

The resistance (Ω) and variation (%) values for each of the nine test points (shown in FIG. 9) are shown in TABLE 1 below.

TABLE 1

Results of the Consistency Testing

| Position Number | 1 | 2 | 3 | 4 | 5 | 6 | 7 | 8 | 9 |
|---|---|---|---|---|---|---|---|---|---|
| Resistance (Ω) | 50.3 | 52.0 | 46.8 | 50.3 | 45.9 | 45.1 | 48.0 | 51.8 | 50.7 |
| Variation (%) | 2.7 | 6.2 | 4.4 | 2.7 | 6.2 | 8.0 | 2.0 | 5.6 | 3.4 |

As shown in TABLE 1, there were some differences in the pressure sensitivity between the nine test points. The largest resistance difference of these nine test points was 8.0%. Although the consistency of the material was not perfect, the material is sufficient for applications focusing on pressure distribution patterns, rather than accurate pressure values.

Testing the Influence of Trimming on the Customizable Pressure Sensor Array

Figure 15:
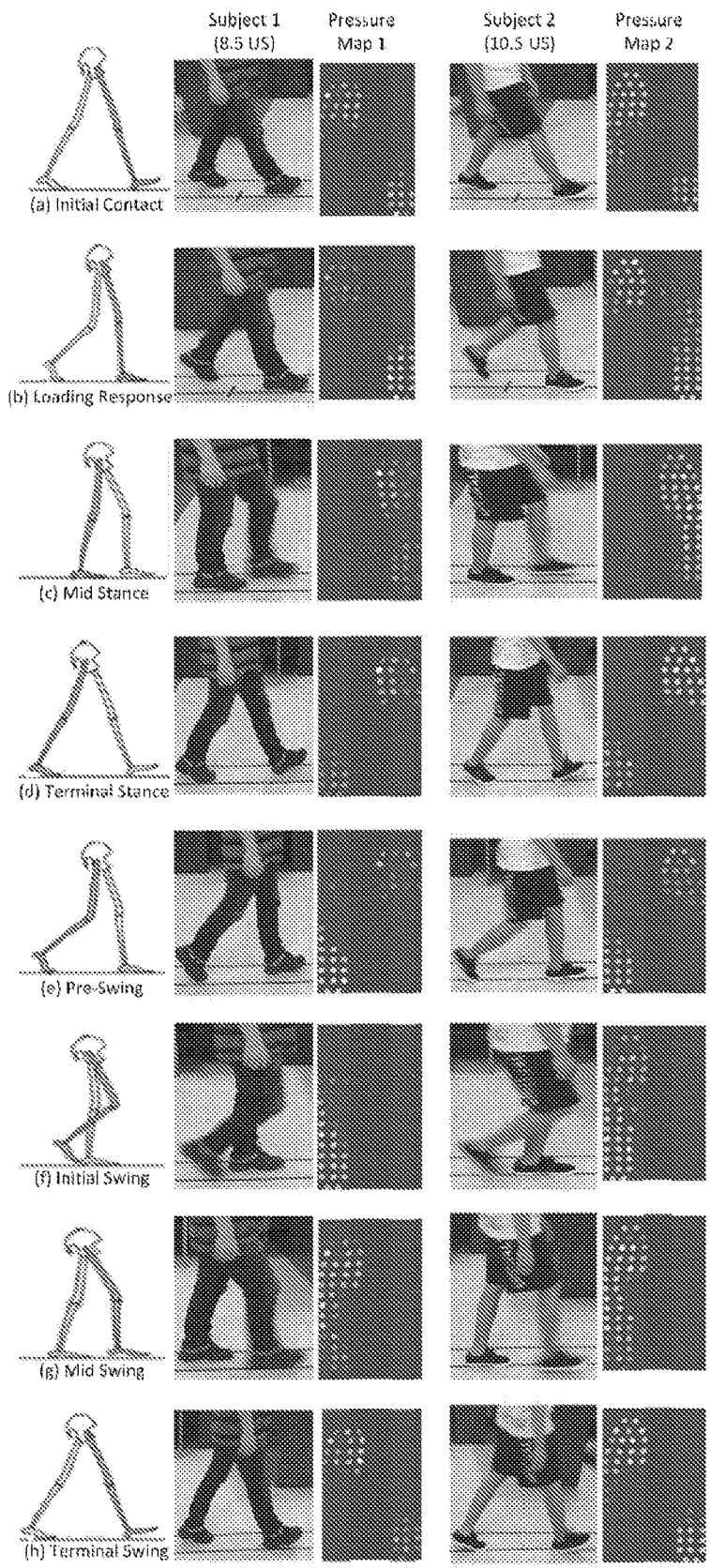
FIG. 15 illustrates experimental results for eight gait phases of each subject and the corresponding plantar pressure distribution map.

FIG. 15 shows eight gait phases ((a)-(h)) of each subject and the corresponding plantar pressure distribution maps. For gait cycle, all of the eight gait phases were found in the tapped videos according to the standard postures shown in FIG. 15. Then the plantar pressure distribution map corresponding to each gait phase was extracted. To evaluate the plantar pressure distribution map acquired by the customizable sensor array, a standard plantar pressure distribution map of each gait phase is necessary. For normal walking, the standard plantar pressure could be acquired by analyzing the posture in each gait phase. Taking the "Initial contact" phase for example, heel of the shaded foot in FIG. 15 starts to contact the ground. At this gait phase, plantar pressure of the shaded foot should concentrate on the heel area. On the contrary, plantar pressure of the contralateral foot should concentrate on the forefoot area. Finally, through comparing the measured plantar pressure distribution map with the standard plantar pressure distribution map, the performance of the customizable pressure sensor array could be evaluated.

Through comparing the standard plantar pressure distribution map with the pressure map acquired by the customizable pressure sensor array, it is obvious that the pressure distribution maps acquired with trimmed and non-trimmed sensor array are both correct for different gait phases. Taking the "Pre-swing" phase for example, only toes of the shaded foot touch the ground, and forefoot and heel of the contralateral foot starts to contact the ground. At this gait phase, there would be a little pressure on the toe area of the shaded foot. While on the contralateral foot, the pressure would be distributed on both forefoot and heel, but more pressure on heel. This is the same as the pressure distribution map acquired with both customizable sensor arrays: there is a little pressure on the right forefoot and a little pressure on the left forefoot, and more pressure is concentrated on the left heel. In addition, it is obvious that the trimmed sensors (in the toe area) are helpful to reveal the pressure distribution pattern.

For the experiment about cadence, the step cycle was calculated as the time difference between the "pre-swing" phase of one foot and the successive "pre-swing" phase of the other foot. Since the subject might need time to walk in a stable cadence, 10 successive steps in the middle (from 10 s to 20 s) of each experiment were used to calculate the mean step cycle and then cadence.

When the cadence was 50 BPM, the cadence was calculated to be 50.3 for the 8.5 US size and 49.1 for the 10.5 US size. When the cadence was 60 BPM, the cadence was calculated to be 59.0 for the 8.5 US size and 59.8 for the 10.5 US size. When the cadence was 70 BPM, the cadence was calculated to be 70.5 for the 8.5 US size and 69.6 for the 10.5 US size. The results show that both insole sizes could be used to extract cadence with high accuracy. The errors might be caused by the variance of walking cadence when the subjects were doing the experiment. The results indicate that trimming has no influence on the pressure spatial and temporal distribution patterns acquired by customizable pressure sensor array.

From the above description, those skilled in the art will perceive improvements, changes and modifications. Such improvements, changes and modifications are within the skill of one in the art and are intended to be covered by the appended claims.

The following is claimed:
1. A system comprising:
   a device housing a pressure sensor array,
      wherein the pressure sensor array comprises a piezo-resistive material and a uniform distribution of a plurality of flexible circuits;
      wherein each of the plurality of flexible circuits comprise at least one wire connected to a common port;
      wherein the device and the pressure sensor array are customizable to different sizes for gait analysis and/or tactile sensing applications; and
      wherein each of the at least one wire from each of the plurality of flexible circuits is positioned to ensure that each of the plurality of flexible circuits is connected to the common port even when customized so that every one of the plurality of flexible circuits remaining on the pressure sensor array as full flexible circuits and partial flexible circuits is usable after the pressure sensor array is customized; and
   a signal processing circuit to estimate a force applied to the pressure sensor array based on a resistance of each portion of the pressure sensor array represented by a pair of flexible circuits,
      wherein the signal processing circuit comprises at least one multiplexer, a voltage divider circuit, an analog-to-digital convertor, a control unit, a power management unit, and a data transmission unit, and wherein the signal processing circuit calculates the resistance of each portion of the pressure sensor array represented by the pair of flexible circuits based on a resistance of a fixed resistor of the voltage divider circuit multiplied by a ratio of a voltage of the portion of the pressure sensor array and a difference between a source voltage of the voltage divider circuit and the voltage of the portion of the pressure sensor array.

2. The system of claim 1, wherein the pressure sensor array retains an original pressure sensing resolution after being customized to the different sizes due to the uniform distribution of the plurality of flexible circuits.

3. The system of claim 1, wherein, for each of the plurality of flexible circuits, the at least one wire connects to an internal portion of a respective flexible circuit.

4. The system of claim 1, wherein the device comprises a shoe insole or a body molding housing.

5. The system of claim 1, wherein the piezo-resistive material is a piezo-resistive fabric and the plurality of flexible circuits each comprise at least one electronic device on a flexible polymer substrate material.

6. The system of claim 5, wherein the at least one electronic device of each of the plurality of flexible circuits comprises at least one copper pad.

7. The system of claim 1, wherein the pressure sensor array comprises a middle layer of the piezo-resistive material surrounded by a top layer comprising a portion of the uniform distribution of the plurality of flexible circuits and a bottom layer comprising an equal portion of the uniform distribution of the plurality of flexible circuits.

8. The system of claim 7, wherein the bottom layer connects the middle layer to a ground electronic level and the top layer connects the middle layer to a source voltage via a fixed resistance.

9. The system of claim 7, wherein the piezo-resistive material has a variable resistance that varies proportionally with an applied pressure.

10. A method comprising:
trimming a device housing a pressure sensor array to a size, wherein the pressure sensor array comprises a piezo-resistive material and a uniform distribution of a plurality of flexible circuits, wherein each of the plurality of flexible circuits comprise at least one wire connecting an internal portion of a respective flexible circuit to a common port; and
using the customized pressure sensor array for a gait analysis and/or tactile sensing application;
connecting the common port to at least one multiplexer for signal processing, wherein the signal processing comprises:
estimating a pressure based on data received from the pressure sensor array based on a variable resistance of the piezo-electric material in the pressure sensor array.

11. The method of claim 10, wherein the variable resistance of the piezo-resistive material varies proportionally with an applied pressure.

12. The method of claim 10, wherein the pressure sensor array retains an original pressure sensing resolution after the trimming due to the uniform distribution of the plurality of flexible circuits.

13. The method of claim 10, wherein each of the plurality of flexible circuits comprise at least one wire connected to a common port; and
wherein each of the at least one wire from each of the plurality of flexible circuits is positioned to ensure that each of the plurality of flexible circuits is connected to the common port even after the trimming so that every one of the plurality of flexible circuits remaining on the sensor array as full flexible circuits and partial flexible circuits are usable after the pressure sensor array is customized.

* * * * *